(12) United States Patent
Gao et al.

(10) Patent No.: US 6,258,595 B1
(45) Date of Patent: Jul. 10, 2001

(54) COMPOSITIONS AND METHODS FOR HELPER-FREE PRODUCTION OF RECOMBINANT ADENO-ASSOCIATED VIRUSES

(75) Inventors: Guang-Ping Gao, Havertown; James M. Wilson, Gladwyne, both of PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/404,555

(22) Filed: Sep. 23, 1999

Related U.S. Application Data

(63) Continuation-in-part of application No. PCT/US99/05870, filed on Mar. 18, 1999.

(51) Int. Cl.⁷ .......................... C12N 15/86; C12N 15/00; C12N 5/00; C07H 21/04; A61K 48/00
(52) U.S. Cl. .................. 435/320.1; 435/325; 435/239; 435/455; 435/466; 536/23.1; 514/44
(58) Field of Search ................. 435/320.1, 239, 435/325, 455, 456; 536/23.1; 514/44

(56) References Cited

U.S. PATENT DOCUMENTS

| | | | |
|---|---|---|---|
| 5,436,146 | 7/1995 | Shenk et al. | 435/457 |
| 5,622,856 | 4/1997 | Natsoulis | 435/325 |
| 5,658,776 | 8/1997 | Flotte et al. | 435/457 |
| 5,658,785 | 8/1997 | Johnson | 435/367 |
| 5,681,731 | 10/1997 | Lebkowski et al. | 435/457 |
| 5,756,283 | 5/1998 | Wilson et al. | 435/5 |
| 5,856,152 | 12/1998 | Wilson et al. . | |
| 5,871,982 | 4/1999 | Wilson et al. . | |

FOREIGN PATENT DOCUMENTS

| | | |
|---|---|---|
| WO 95/06743 | 3/1995 | (WO) . |
| WO 96/13598 | 5/1996 | (WO) . |
| WO 96/14061 | 5/1996 | (WO) . |
| WO 96/39530 | 12/1996 | (WO) . |
| WO 96/40240 | 12/1996 | (WO) . |
| WO 97/17458 | 5/1997 | (WO) . |
| WO 98/09657 | 3/1998 | (WO) . |
| WO 98/10086 | 3/1998 | (WO) . |
| WO 98/10088 | 3/1998 | (WO) . |
| WO 99/14354 | 3/1999 | (WO) . |
| WO 99/15685 | 4/1999 | (WO) . |

OTHER PUBLICATIONS

Berendsen, Herman J. "A Glimpse of the Holy Grail", Science 282, pp. 642–643, Oct. 1998.*
B.J. Carter, in "Handbook of Parvoviruses", ed. P. Tijsser, CRC Press, pp. 155–168 (1990).
R. Kotin, "Prospects for the Use of Adeno–Associated Virus as a Vector for Human Gene Therapy", *Hum. Gen Ther.*, 5:793–801 (Jul. 1994).
G–P. Gao et al., "High Titer Adeno–Associated Viral Vectors from a Rep/Cap Cell Line and Hybrid Shuttle Vector", *Hum. Gene Ther.*, 9(16): 2353–2362 (Nov. 1, 1998).
D.D. Coovert et al., "Gene Therapy for Muscle Diseases", *Curr. Opin. Neurol.*, 7(5): 463–470 (Oct. 1, 1994).

* cited by examiner

*Primary Examiner*—Robert A. Schwartzman
*Assistant Examiner*—Gerald G. Leffers, Jr.
(74) *Attorney, Agent, or Firm*—Howson & Howson

(57) ABSTRACT

A method for producing recombinant adeno-associated virus in the absence of contaminating helper virus or wild-type virus involves culturing a mammalian host cell containing an rAd/AAV hybrid virus, an AAV rep sequence and an AAV cap sequence under the control of regulatory sequences directing expression thereof. The rAd/AAV hybrid virus contains a rAAV construct to be packaged into an AAV virion in a backbone containing the adenoviral sequences necessary to express E1a and E1b gene products and to permit replication of the hybrid virus. The method of the invention permits replication of the hybrid virus and production of rAAV virion in this host cell in the absence of a helper virus and obviates a subsequent purification step to purify rAAV from contaminating virus.

22 Claims, 2 Drawing Sheets

COMPOSITIONS AND METHODS FOR HELPER-FREE PRODUCTION OF RECOMBINANT ADENO-ASSOCIATED VIRUSES

CROSS-REFERENCE TO RELATED APPLICATIONS

This is a continuation-in-part of International Patent Application PCT/US99/05870, filed Mar. 18, 1999.

BACKGROUND OF THE INVENTION

Adeno-associated virus (AAV) is a replication-deficient parvovirus, the genome of which is about 4.6 kb in length, including 145 nucleotide inverted terminal repeats (ITRs). Two open reading frames encode a series of rep and cap polypeptides. Rep polypeptides (rep78, rep68, rep62 and rep40) are involved in replication, rescue and integration of the AAV genome. The cap proteins (VP1, VP2 and VP3) form the virion capsid. Flanking the rep and cap open reading frames at the 5' and 3' ends are 145 bp inverted terminal repeats (ITRs), the first 125 bp of which are capable of forming Y- or T-shaped duplex structures. Of importance for the development of AAV vectors, the entire rep and cap domains can be excised and replaced with a therapeutic or reporter transgene [B. J. Carter, in "Handbook of Parvoviruses", ed., P. Tijsser, CRC Press, pp.155–168 (1990)]. It has been shown that the ITRs represent the minimal sequence required for replication, rescue, packaging, and integration of the AAV genome.

When this nonpathogenic human virus infects a human cell, the viral genome integrates into chromosome 19 resulting in latent infection of the cell. Production of infectious virus and replication of the virus does not occur unless the cell is coinfected with a lytic helper virus, such as adenovirus (Ad) or herpesvirus. Upon infection with a helper virus, the AAV provirus is rescued and amplified, and both AAV and helper virus are produced. The infecting parental ssDNA is expanded to duplex replicating form (RF) DNAs in a rep dependent manner. The rescued AAV genomes are packaged into preformed protein capsids (icosahedral symmetry approximately 20 nm in diameter) and released as infectious virions that have packaged either + or − ss DNA genomes following cell lysis.

AAV possesses unique features that make it attractive as a vector for delivering foreign DNA (i.e., a transgene) to cells, and various groups have studied the potential use of AAV in the treatment of disease states. As used in this application, the term "transgene" means the DNA desired to be delivered to an animal, the DNA being non-AAV DNA. However, progress towards establishing AAV as a transducing vector for the delivery of DNA in the form of a desired transgene has been slow for a variety of reasons.

One obstacle to the use of AAV for delivery of DNA has been lack of highly efficient schemes for encapsidation of recombinant genomes and production of infectious virions. See, R. Kotin, *Hum. Gene Ther.*, 5:793–801 (1994)]. One method which addresses this problem involves transfecting a recombinant AAV (rAAV) (which has the DNA to be delivered, but lacks rep and cap genes) into host cells followed by co-infection with wild-type (wt) AAV (which supplies the rep and cap genes) and adenovirus (which supplies at least the four adenovirus genes: E1, E2, E4 and VAI, which have been stated to be necessary for rAAV production) [see, e.g., Carter, cited above]. However, this method requires mandatory co-infection and leads to unacceptably high levels of wt AAV resulting from non-homologous recombination and contamination of the rAAV produced with wt AAV. The contamination with other viruses or plasmids demands purification of rAAV. Incubation of cells with rAAV in the absence of contaminating wt AAV or helper adenovirus yields little recombinant gene expression.

A widely recognized means for manufacturing transducing AAV virions for gene therapy entails co-transfection with two different, complementing plasmids. One of these plasmids contains a therapeutic or reporter transgene sandwiched between the two cis acting AAV ITRs. The AAV components that are needed for rescue and subsequent packaging of progeny recombinant genome are provided in trans by a second plasmid encoding the viral open reading frames for rep and cap proteins. In this system, the Ad helper functions are provided by a wt adenovirus or by replication-defective adenovirus with the missing E1 gene supplied by HEK 293 cells. Other variants of this method have been described. See, for example, U.S. Pat. No. 5,658,785, which refers to a mammalian host cell stably transfected with a rAAV genome and with AAV rep and cap genes, and a method for producing rAAV by infecting this host cell with a helper virus.

U.S. Pat. No. 5,658,776 refers to packaging systems and processes for packaging AAV vectors in which the AAV p5 promoter is replaced with a heterologous promoter. Alternatively, U.S. Pat. No. 5,622,856 refers to constructs and methods for AAV vector production in which the homologous p5 promoter is moved to a position 3' of the rep genes, optionally flanking the rep/cap genes and repositioned p5 promoter with FRT sequences.

There remains a need in the art for additional compositions and methods permitting the efficient production of AAV and recombinant AAV viruses for use as vectors for somatic gene therapy without the inefficiency, contamination and purification problems present in the methods previously described.

SUMMARY OF THE INVENTION

The present invention allows for the efficient production of rAAV containing a desired transgene DNA. Particularly, the present invention provides both compositions and methods which enable the production of a rAAV without the problem of homologous recombination which produces contaminating re-assembled wt AAV during rAAV production.

In one aspect, the invention provides a replication-competent hybrid adenovirus/AAV virus containing a recombinant adeno-associated viral (rAAV) vector and sufficient adenoviral sequences to permit replication of said hybrid virus in a selected host cell. In one embodiment, the hybrid virus contains a functional deletion in the wild-type adenoviral E3 region and/or a non-functional deletion of adenoviral sequences in the E4 region, such that the hybrid virus contains an adenoviral E4 ORF6 region.

In another aspect, the invention provides an adenovirus/AAV hybrid virus containing (a) adenovirus 5' cis-elements necessary for replication and packaging; (b) a recombinant adeno-associated viral (rAAV) vector; (c) a deletion of adenoviral sequences from the E3 region; (d) nucleic acid sequences encoding adenovirus E1a and adenovirus E1b under the control of regulatory sequences directing expression of the E1a and E1b gene products, wherein said E1a and E1b nucleic acid sequences are located in the site of the E3 region and; (e) adenovirus 3' cis-elements necessary for replication and packaging. In one suitable embodiment, the hybrid virus provides all sequences necessary to provide helper function for packaging the rAAV.

In another aspect, a method for producing recombinant adeno-associated virus (rAAV) in the absence of contaminating helper virus or wild-type virus, comprising the step of culturing a host cell comprising a replication-competent rAd/AAV and an AAV rep sequence and an AAV cap sequence under the control of regulatory sequences directing expression thereof. Suitably, the method further involves the step of controlling replication of the rAd/AAV hybrid following infection, thereby enhancing production of rAAV. In a preferred embodiment, the method of the invention simplifies purification steps because the replication-competent rAd/AAV provides the rAAV construct to be packaged and all necessary adenoviral sequences, there is no helper virus used and there is insufficient adenovirus sequence in the host cell to permit homologous recombination to a contaminating wt virus.

Other aspects and advantages of the present invention are described further in the following detailed description of the preferred embodiments thereof.

BRIEF DESCRIPTION OF THE INVENTION

1. E1-Expressing Adenovirus/AAV Hybrid Virus

Figure 1A:
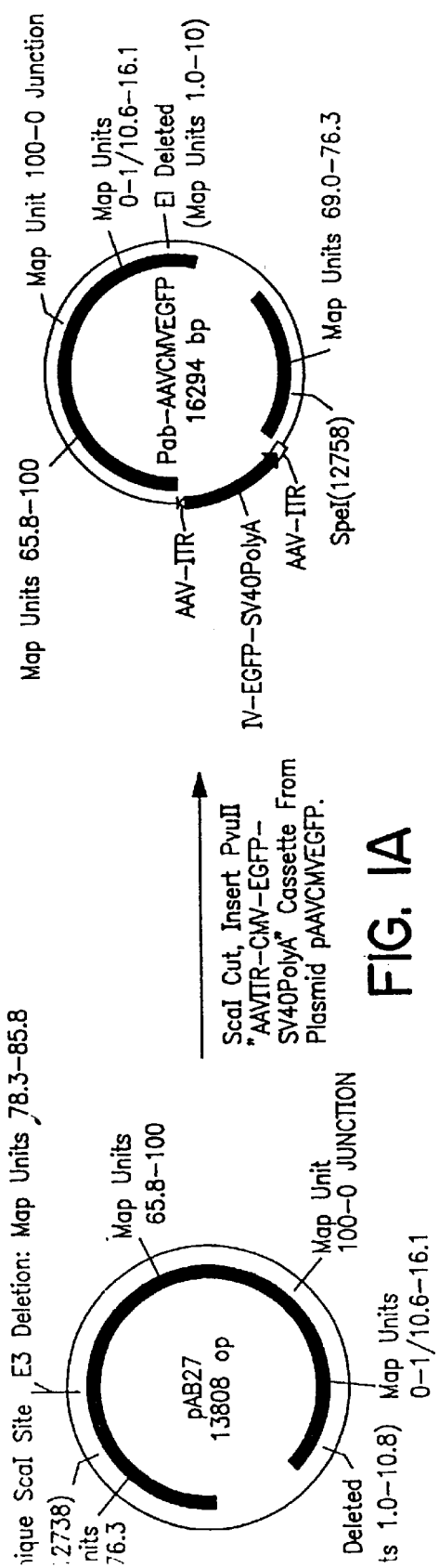
FIGS. 1A–1B are a schematic map illustrating production of a replication-competent rAd/AAV hybrid virus.

The present invention provides a recombinant adenovirus/AAV (rAd/AAV) hybrid virus, in which an adenovirus is engineered to contain a rAAV construct to be packaged into a rAAV virion and sufficient adenoviral sequences to permit replication of said hybrid virus in a selected host cell. In a preferred embodiment, all the necessary adenoviral genes are provided by the rAd/AAV hybrid virus, which may lack the adenoviral sequences from the wild-type E3 and may contain non-functional deletions of adenoviral sequences, e.g., the hybrid virus may lack all adenoviral E4 coding sequences with the exception of the sequences necessary to express the E4 ORF6 function. The rAAV construct may be inserted into either the adenovirus E3 or the E1 region. Optionally, the sequences encoding the E1 gene products are inserted into and expressed from the wild-type E3 region. In another embodiment, the invention provides a rAd/AAV expressing the E1 gene products, but which lack one or more of the other necessary adenoviral sequences (e.g., E2a and/or E4 ORF6), which is supplied by the host cell. The hybrid virus of the invention, described in detail below, is useful for production of rAAV in a host cell which contains, at a minimum, an AAV rep sequence and an AAV cap sequence under the control of regulatory sequences directing expression thereof.

A. Adenoviral Gene Sequences

At a minimum, the adenovirus sequences employed in the rAd/AAV hybrid virus of the invention are the cis-acting 5' and 3' inverted terminal repeat (ITR) sequences of an adenovirus (which function as origins of replication), the native 5' packaging/enhancer domain, that contains sequences necessary for packaging linear Ad genomes and enhancer elements for the E1 promoter, and the DNA necessary to permit replication of the hybrid virus in a selected host cell. Most preferably, all necessary adenovirus gene products, i.e., E1a, E1b, E2a, E2b, E4 ORF6, the adenoviral intermediate genes IX and IXa, and adenoviral late genes L1, L2, L3, L4 and L5 are expressed from the hybrid virus. The adenovirus sequences may be derived from one or more wild-type adenoviruses or a mutant adenoviruses.

The DNA sequences encoding the adenoviral genes useful in this invention may be selected from among any known adenovirus type, including the presently identified 46 human types [see, e.g., Horwitz, cited above and American Type Culture Collection]. Similarly, adenoviruses known to infect other animals may supply the gene sequences. The selection of the adenovirus type for each E1 and E2a gene sequence does not limit this invention. The sequences for a number of adenovirus serotypes, including that of serotype Ad5, are available from Genbank. A variety of adenovirus strains are available from the American Type Culture Collection (ATCC), Manassas, Va., or are available by request from a variety of commercial and institutional sources. Any one or more of human adenoviruses Types 1 to 46 may supply any of the adenoviral sequences. In the following exemplary embodiment the E1 and E2a gene sequences are those from adenovirus serotype 5 (Ad5).

As used herein by "DNA which expresses the gene product", it is meant any nucleic acid sequence the gene product or any functional portion thereof. Similarly included are any alleles or other modifications of the nucleic acid sequence (e.g., a gene) or functional portion thereof. As defined herein, "functional portion or functional fragment" is that region of coding sequence or gene product which is required to provide the necessary desired function. Such modifications may be deliberately introduced by resort to conventional genetic engineering or mutagenic techniques to enhance the function of the gene product(s) in some manner, as well as naturally occurring allelic variants thereof.

In a preferred embodiment, the rAd/AAV hybrid virus of the invention lacks the sequences encoding the adenoviral E3 gene product, thus enabling a heterologous sequence to be inserted into the native E3 region, which is non-essential for replication and infection. Such a heterologous sequence may be any nucleic acid sequence which is not native to the adenovirus, or any nucleic acid sequence from a non-contiguous region of the same adenovirus. Similarly, the rAd/AAV hybrid virus may lack adenoviral E4 coding sequences with the exception of E4 ORF6 which is essential. Suitably, the rAd/AAV hybrid virus is engineered such that it does not exceed 105% of the size of the native adenoviral genome (e.g., 105% of 36 kb). Thus, where desired, e.g., to permit insertion of a desired heterologous sequence, the rAd/AAV may be engineered to contain other non-functional deletions of sequences wild-type to the adenovirus(es) from which the hybrid is engineered. Such non-functional deletions include those which do not extinguish the ability of the hybrid virus to express a functional gene product required for replication of the hybrid virus. The deletion of all adenoviral E4 coding sequences with the exception of the E4 ORF6 sequences is an example of a non-functional deletion. Other suitable non-functional deletions may be readily designed.

Thus, in particularly desirable embodiment, all the necessary adenoviral genes for replication of the rAd/AAV hybrid virus are provided by the hybrid virus itself. Such a hybrid virus contains a rAAV construct to be packaged into a virion, lacks adenoviral sequences encoding adenovirus E3, and lacks all adenoviral E4 coding sequences with the exception of E4 ORF6 function. Optionally, the adenoviral E1a and E1b gene products may be expressed from a region other than the wild-type E1 region, e.g., these gene products are inserted into and expressed from the wild-type E3 region.

In another embodiment, the rAd/AAV of the invention lacks one or more of the other adenoviral genes required for replication. Any required adenoviral gene products which have been deleted from the hybrid virus can be supplied in the production process by a selected packaging cell or in trans by a nucleic acid sequence directing expression of the desired gene product. Preferably, the rAd/AAV expresses the E1a and E1b gene products. In one example, the rAd/AAV hybrid virus contains wild-type E1 functions, but lacks the sequences necessary for expression of E4 ORF6. In this situation, the rAd/AAV hybrid is introduced into a host cell which contains the sequences necessary for expressing E4 ORF6. In another example the rAd/AAV hybrid virus lacks the sequences necessary for expression of E2a, which function is expressed in the host cell used for production of the rAAV. Such host cells are discussed in more detail below.

Design of these and other rAd/AAV hybrid viruses within the scope of this invention includes appropriate sequences that are operably linked to the gene of interest to promote its expression. "Operably linked" sequences include both expression control sequences that are contiguous with the gene of interest and expression control sequences that act in trans or at a distance to control the gene of interest. Such expression control sequences are discussed in more detail in connection with the transgene.

The promoters for each of the adenoviral genes may be selected independently from a constitutive promoter, an inducible promoter or a native adenoviral promoter (i.e., a promoter may be one which is naturally associated with the 5' flanking region of an adenovirus gene). The promoters may be regulated by a specific physiological state of the organism or cell (i.e., by the differentiation state or in replicating or quiescent cells) or by exogenously-added factors, for example. The selected promoters may be identical or may be different.

In one embodiment, the E1a gene (and subsequently the E1b gene) is expressed under the control of a constitutive promoter, including, without limitation, the RSV LTR promoter/enhancer, the CMV immediate early promoter/enhancer, the SV40 promoter, the dihydrofolate reductase promoter, the cytoplasmic β-actin promoter and the phosphoglycerol kinase (PGK) promoter.

In another embodiment, an inducible promoter is employed to express the E1 gene products, so as to control the amount and timing of the cell's production of the E1a and E1b gene products, which can be toxic to the cell upon excessive accumulation [see, e.g., William S. M. Wold, *J. Cell Biochem.*, 53:329–335 (1993); J. Nevins, *Current Opinion in Genetics and Development*, 4:130–134 (1994); E. Harrington et al, *Current Opinion in Genetics and Development*, 4:120–129 (1994); G. Evan et al, *Current Opinion in Cell Biology*, 7:825–834 (1995); J. Nevins, *Science*, 258:424 (1992)]. Inducible promoters include those known in the art and those discussed above including, without limitation, the zinc-inducible sheep metallothionine (MT) promoter; the dexamethasone (Dex)-inducible mouse mammary tumor virus (MMTV) promoter; the T7 promoter; the ecdysone insect promoter; the tetracycline-repressible system; the tetracycline-inducible system; the RU486-inducible system; and the rapamycin-inducible system. Any type of inducible promoter which is tightly regulated and which provides for high-level expression of E1 may be used. Other types of inducible promoters which may be useful in this context are those which are regulated by a specific physiological state, e.g., temperature, acute phase, a particularly differentiation state of the cell, or in replicating cells only.

B. Recombinant AAV Construct

In the rAd/AAV virus, the AAV sequences are inserted into the adenoviral backbone in a region deleted of native adenoviral sequence, and thus are flanked by the selected adenoviral sequences. The AAV sequences are typically in the form of a rAAV construct (e.g., a cassette) which is packaged into a rAAV virion according to the method of the invention. The rAAV construct contains, at a minimum (from 5' to 3'), 5' AAV ITR sequences, a selected transgene under the control of a selected promoter and other conventional vector regulatory components, and 3' AAV ITR sequences. Each of these components of the rAAV construct is discussed below. See, also, U.S. Pat. Nos. 5,856,152 and 5,871,982. One of skill in the art can readily engineer the rAd/AAV hybrid virus so as to insert the rAAV construct into the desired adenoviral region. In one embodiment, the rAAV construct is located in the adenoviral E3 region of the rAd/AAV hybrid virus. In another suitable embodiment, the rAAV construct is located in the adenoviral E1 region of the rAd/AAV hybrid virus. However, the present invention is not limited to these exemplary embodiments.

1. AAV Sequences

The AAV sequences employed are preferably the cis-acting 5' and 3' inverted terminal repeat sequences [See, e.g., B. J. Carter, in "Handbook of Parvoviruses", ed., P. Tijsser, CRC Press, pp.155–168 (1990)]. The ITR sequences are about 145 bp in length. Preferably, substantially the entire sequences encoding the ITRs are used in the molecule, although some degree of minor modification of these sequences is permissible. The ability to modify these ITR sequences is within the skill of the art. [See, e.g., texts such as Sambrook et al, "Molecular Cloning. A Laboratory Manual", 2d ed., Cold Spring Harbor Laboratory, New York (1989); Carter et al, cited above; and K. Fisher et al., *J. Virol.*, 70:520–532 (1996)]. An example of such a molecule employed in the present invention is a "cis-acting" plasmid containing the transgene, in which the selected transgene sequence and associated regulatory elements are flanked by the 5' and 3' AAV ITR sequences.

The AAV ITR sequences may be obtained from any known AAV, including presently identified human AAV types. Similarly, AAVs known to infect other animals may also provide these ITRs employed in the molecules or constructs of this invention. For example, the ITRs may be provided by AAV type 1, AAV type 2, AAV type 3, AAV type 4, AAV type 5, AAV 6, other AAV serotypes or densovirus. A variety of AAV strains are available from the American Type Culture Collection or are available by request from a variety of commercial and institutional sources. In the following exemplary embodiments an AAV-2 is used for convenience. However, the selection of the species and serotype of AAV that provides these sequences is within the skill of the artisan according to the teachings of this application and does not limit the following invention.

2. Transgene

According to the present invention, the rAAV construct contains a nucleic acid molecule which comprises a desired transgene, a promoter, and other regulatory elements which control and direct expression of the transgene in a host cell, flanked by AAV sequences. The transgene sequence is a nucleic acid sequence, heterologous to the AAV sequence, which encodes a polypeptide or protein of interest. The composition of the transgene sequence depends upon the intended use for the resulting rAAV. For example, one type of transgene sequence comprises a reporter or marker sequence, which upon expression produces a detectable signal. Such reporter or marker sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed to them exist or can be made routinely, and fusion proteins comprising a membrane bound protein appropriately fused to an antigen tag domain from, among others, hemagglutinin or Myc.

These sequences, when associated with regulatory elements which drive their expression, provide signals detectable by conventional means, including enzymatic, radiographic, colorimetric, fluorescence or other spectrographic assays, fluorescent activated cell sorting assay and immunological assays, including ELISA, RIA and immunohistochemistry. For example, where the transgene is the LacZ gene, the presence of rAAV is detected by assays for beta-galactosidase activity. Similarly, where the transgene is luciferase, rAAV may be measured by light production in a luminometer.

However, desirably, the transgene is a non-marker gene which can be delivered to a cell or an animal via the rAAV produced by this method. The transgene may be selected from a wide variety of gene products useful in biology and medicine, such as proteins, antisense nucleic acids (e.g., RNAs), or catalytic RNAs. The invention may be used to correct or ameliorate gene deficiencies, wherein normal genes are expressed but at less than normal levels, and may also be used to correct or ameliorate genetic defects wherein a functional gene product is not expressed. A preferred type of transgene sequence is a therapeutic gene which expresses a desired gene product in a host cell. These therapeutic nucleic acid sequences typically encode products which, upon expression, are able to correct or complement an inherited or non-inherited genetic defect, or treat an epigenetic disorder or disease. However, the selected transgene may encode any product desirable for study. The selection of the transgene sequence is not a limitation of this invention. Choice of a transgene sequence is within the skill of the artisan in accordance with the teachings of this application.

The invention also includes methods of producing rAAV which can be used to correct or ameliorate a gene defect caused by a multi-subunit protein. In certain situations, a different transgene may be used to encode each subunit of the protein. This is desirable when the size of the DNA encoding the protein subunit is large, e.g., for an immunoglobulin or the platelet-derived growth factor receptor. In order for the cell to produce the multi-subunit protein, a cell would be infected with rAAV containing each of the different subunits. Alternatively, different subunits of a protein may be encoded by the same transgene. In this case, a single transgene would include the DNA encoding each of the subunits, with the DNA for each subunit separated by an internal ribosome entry site (IRES). This is desirable when the size of the DNA encoding each of the subunits is small, such that the total of the DNA encoding the subunits and the IRES is less than five kilobases.

Useful gene products include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factors (CTGF), basic fibroblast growth factor (bFGF), acidic fibroblast growth factor (aFGF), epidermal growth factor (EGF), transforming growth factor α (TGFα), platelet-derived growth factor (PDGF), insulin-like growth factors I and II (IGF-I and IGF-II), any one of the transfomiing growth factor β (TGFβ) superfamily comprising TGFβ, activins, inhibins, or any of the bone morphogenic proteins (BMP) BMPs 1–15, any one of the heregulin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful gene products include proteins that regulate the immune system including, without limitation, cytokines and lymphokines such as thrombopoietin (TPO), interleukins (IL) IL-1α, IL-1β, IL-2, IL-3, IL4, IL-5, IL-6, IL-7, IL-8, IL-9, IL-10, IL-11, IL-12, IL-13, IL-14, IL-15, IL- 16, and IL-17, monocyte chemoattractant protein (MCP-1), leukemia inhibitory factor (LIF), granulocyte-macrophage colony stimulating factor (GM-CSF), Fas ligand, tumor necrosis factors α and β (TNFα and TNFβ), interferons (IFN) IFN-α, IFN-β and IFN-γ, stem cell factor, flk-2/flt3 ligand. Gene products produced by the immune system are also encompassed by this invention. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered MHC molecules including single chain MHC molecules. Use gene products also include complement regulatory proteins such as complement regulatory proteins, membrane cofactor protein (MCP), decay accelerating factor (DAF), CR1, CR2 and CD59.

Still other useful gene products include any one of the receptors for the hormones, growth factors, cytokines, lymphokines, regulatory proteins and immune system proteins. The invention encompasses receptors for cholesterol regulation, including the LDL receptor, HDL receptor, VLDL receptor, and the scavenger receptor. The invention also encompasses gene products such as steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP-2, myb, MRG1, CREM, Alx4, FREAC1, NF-κB, members of the leucine zipper family, C2H4 zinc finger proteins, including Zif268, EGR1, EGR2, C6 zinc finger proteins, including the glucocorticoid and estrogen receptors, POU domain proteins, exemplified by Pit1, homeodomain proteins, including HOX-1, basic helix-loop-helix proteins, including myc, MyoD and myogenin, ETS-box containing proteins, TFE3, E2F, ATF1, ATF2, ATF3, ATF4, ZF5, NFAT, CREB, HNF4, C/EBP, SP1, CCAAT-box binding proteins, interferon regulation factor 1 (IRF-1), Wilms tumor protein, ETS-binding protein, STAT, GATA-box binding proteins, e.g., GATA-3, and the forkhead family of winged helix proteins.

Other useful gene products include carbamoyl synthetase I, ornithine transcarbamylase, arginosuccinate synthetase, arginosuccinate lyase, arginase, fumarylacetoacetate hydrolase, phenylalanine hydroxylase, alpha-1 antitrypsin, glucose-6-phosphatase, low-density-lipoprotein receptor, porphobilinogen deaminase, factor VIII, factor IX, cystathione beta-synthase, branched chain ketoacid decarboxylase, albumin isovaleryl-CoA dehydrogenase, propionyl CoA carboxylase, methyl malonyl CoA mutase, glutaryl CoA dehydrogenase, insulin, beta-glucosidase, pyruvate carboxylase, hepatic phosphorylase, phosphorylase kinase, glycine decarboxylase (also referred to as P-protein), H-protein, T-protein, Menkes disease protein, tumor suppressors (e.g., p53), cystic fibrosis transmembrane regulator (CFTR), and the product of Wilson's disease gene PWD.

Other useful transgenes include non-naturally occurring polypeptides, such as chimeric or hybrid polypeptides or polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a gene.

Design of the transgene for expression in mammalian cells and hosts should include appropriate sequences that are operably linked to the gene of interest to promote its expression. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. A great number of expression control sequences—native, constitutive, inducible and/or tissue-specific—are known in the art and may be utilized to drive expression of the transgene, depending upon the type of expression desired. For eukaryotic cells, expression control sequences typically include a promoter, an enhancer, such as one derived from an immunoglobulin gene, SV40, cytomegalovirus, etc., and a polyadenylation sequence which may include splice donor and acceptor sites. The polyadenylation sequence generally is inserted following the transgene sequences and before the 3' AAV ITR sequence. A rAAV construct useful in the present invention may also contain an intron, desirably located between the promoter/enhancer sequence and the transgene. One possible intron sequence is also derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al, and references cited therein at, for example, pages 3.18–3.26 and 16.17–16.27 and Ausubel et al., *Current Protocols in Molecular Biology*, John Wiley & Sons, New York, 1989].

In one embodiment, high-level constitutive expression will be desired. Examples of such promoters include, without limitation, the retroviral Rous sarcoma virus (RSV) LTR promoter/enhancer, the cytomegalovirus (CMV) immediate early promoter/enhancer [see, e.g., Boshart et al, *Cell*, 41:521–530 (1985)], the SV40 promoter, the dihydrofolate reductase promoter, the cytoplasmic β-actin promoter and the phosphoglycerol kinase (PGK) promoter.

In another embodiment, inducible promoters may be desired. Inducible promoters are those which are regulated by exogenously supplied compounds, including without limitation, the zinc-inducible sheep metallothionine (MT) promoter; the dexamethasone (Dex)-inducible mouse mammary tumor virus (MMTV) promoter, the T7 polymerase promoter system [WO 98/10088]; the ecdysone insect promoter [No et al, *Proc. Natl. Acad. Sci. USA*, 93:3346–3351 (1996)]; the tetracycline-repressible system [Gossen et al, *Proc. Natl. Acad. Sci. USA*, 89:5547–5551 (1992)]; the tetracycline-inducible system [Gossen et al., *Science*, 268:1766–1769 (1995); see also Harvey et al., *Curr. Opin. Chem. Biol.*, 2:512–518 (1998)]; the RU486-inducible system [Wang et al., *Nat. Biotech.*, 15:239–243 (1997) and Wang et al., *Gene Ther.*, 4:432–441 (1997)]; and the rapamycin-inducible system [Magari et al. *J. Clin. Invest.*, 100:2865–2872 (1997)]. Other types of inducible promoters which may be useful in this context are those which are regulated by a specific physiological state, e.g., temperature, acute phase, or in replicating cells only. In a preferred embodiment, the transgene is under the control of the P5 native AAV promoter.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the transgene includes transgene operably linked to a tissue-specific promoter. For instance, if expression in skeletal muscle is desired, a promoter active in muscle should be used. These include the promoters from genes encoding skeletal α-actin, myosin light chain 2A, dystrophin, muscle creatine kinase, as well as synthetic muscle promoters with activities higher than naturally-occurring promoters [see Li et al., *Nat. Biotech.*, 17:241–245 (1999)]. Examples of promoters that are tissue-specific are known for liver [albumin, Miyatake et al. *J. Virol.*, 71:5124–32 (1997); hepatitis B virus core promoter, Sandig et al., *Gene Ther.*, 3:1002–9 (1996); alpha-fetoprotein (AFP), Arbuthnot et al., *Hum. Gene Ther.*, 7:1503–14 (1996)], bone [osteocalcin, Stein et al., *Mol. Biol. Rep.*, 2:185–96 (1997); bone sialoprotein, Chen et al., *J. Bone Miner. Res.*, 1:654–64 (1996)], lymphocytes [CD2, Hansal et al., *J. Immunol.*, 161:1063–8 (1998); immunoglobulin heavy chain; T cell receptor α chain], neuronal [neuron-specific enolase (NSE) promoter, Andersen et al. *Cell. Mol. Neurobiol.*, 13:503–15 (1993); neurofilament light-chain gene, Piccioli et al., *Proc. Natl. Acad. Sci. USA*, 88:5611–5 (1991); the neuron-specific vgf gene, Piccioli et al., *Neuron*, 15:373–84 (1995)]; among others.

Of course, not all vectors and expression control sequences will function equally well to express all of the transgenes of this invention. However, one of skill in the art may make a selection among these expression control sequences without departing from the scope of this invention. Suitable promoter/enhancer sequences may be selected by one of skill in the art using the guidance provided by this application. Such selection is a routine matter and is not a limitation of the molecule or construct. For instance, one may select one or more expression control sequences, operably link the sequence to a transgene of interest, and insert the "minigene" comprising the expression control sequence and the transgene into an AAV vector. After following one of the methods for packaging the rAAV taught in this specification, or as taught in the art, one may infect suitable cells in vitro or in vivo. The number of copies of the transgene in the cell may be monitored by Southern blotting or quantitative PCR; the level of RNA expression may be monitored by Northern blotting or quantitative RT-PCR; and the level of protein expression may be monitored by Western blotting, immunohistochemistry, ELISA, RIA, or tests of the transgene's gene product's biological activity. Thus, one may easily assay whether a particular expression control sequence is suitable for a specific transgene, and choose the expression control sequence most appropriate for expression of the desired transgene.

C. Production of rAd/AAV Hybrid Virus

The rAd/AAV hybrid virus of the invention may be constructed and produced using the materials and methods described herein, as well as those known to those of skill in the art. Such engineering methods used to construct any embodiment of this invention are known to those with skill in nucleic acid manipulation and include genetic engineering, recombinant engineering, and synthetic techniques. See, e.g., Sambrook et al, and Ausubel et al., cited above; and International Patent Application No. WO95/13598. Further, methods suitable for producing a rAAV cassette in an adenoviral capsid have been described in U.S. Pat. Nos. 5,856,152 and 5,871,982.

Because the rAd/AAV hybrid virus of the invention is replication-competent, it may be produced by infection and replication in a selected host cell, using techniques known to those of skill in the art and as described herein. See, U.S. Pat. Nos. 5,856,152 and 5,871,982, and discussion of methods of infecting and culturing a host cell with the rAd/AAV described in Part II below.

II. Production of rAAV

The method of the invention provides for production of rAAV utilizing a replication-competent rAd/AAV. In a particularly preferred embodiment, the rAd/AAV used in the method of the invention provides the rAAV cassette and all necessary adenoviral sequences to the host cell, thus avoiding the need for a second infection or transfection with a helper virus. Most suitably, the rAd/AAV hybrid virus is engineered as described herein so that all adenoviral gene products required for replication of the hybrid virus are expressed by the rAd/AAV hybrid virus.

Briefly, the selected host cell is infected with rAd/AAV hybrid virus. Once the rAd/AAV hybrid virus is taken up by a cell, the AAV ITR flanked transgene must be rescued from the adenovirus backbone by supplying the infected cell with an AAV rep gene, which preferably is present in the host packaging cell. The recombinant AAV genome is packaged by supplying the infected cell with an AAV cap gene, which is preferably present in the host packaging cell.

Regardless of the rAd/AAV used in the production of rAAV, critical to the optimal production of rAAV, the method of the invention includes a step which controls (i.e., inhibits or extinguishes) the ability of the rAd/AAV to replicate at a selected time following infection of the host cells. This step enhances the ability of the rAAV construct carried by the rAd/AAV to be rescued and packaged into a rAAV virion. This may be achieved by a variety of means, which are described in more detail herein.

A. AAV Rep and Cap Sequences

In order to package the rAAV construct provided by the rAd/AAV hybrid into a rAAV virion, a host cell must contain sequences necessary to express AAV rep and AAV cap or functional fragments thereof For example, the rep78/52 proteins may be sufficient to provide the necessary rep functions. The AAV rep and cap sequences are obtained from an AAV source as identified above. The AAV rep and cap sequences may be introduced into the host cell in any manner known to one in the art as described above, including, without limitation, transfection, electroporation, liposome delivery, membrane fusion techniques, high velocity DNA-coated pellets, viral infection and protoplast fusion. In one embodiment, the rep and cap sequences may be transfected into the host cell by one or more nucleic acid molecules and exist stably in the cell as an episome. In another embodiment, the rep and cap sequences are stably integrated into the genome of the cell. A stable host cell line that contains rep and cap is B-50, described in PCT/US98/19463. Another embodiment has the rep and cap sequences transiently expressed in the host cell. For example, a useful nucleic acid molecule for such transfection comprises, from 5' to 3', a promoter, an optional spacer interposed between the promoter and the start site of the rep gene sequence, an AAV rep gene sequence, and an AAV cap gene sequence.

The rep and cap sequences, along with their expression control sequences, may be supplied on a single vector, or each sequence may be supplied on its own vector. Preferably, the rep and cap sequences are supplied on the same vector. Alternatively, the rep and cap sequences may be supplied on a vector that contains other DNA sequences that are to be introduced into the host cells.

Preferably, the promoter used in this construct may be any of the constitutive, inducible or native promoters known to one of skill in the art or as discussed above. In a preferred embodiment, an AAV P5 promoter sequence is employed. While it may be obtained from any of the above-mentioned AAV sources, the parvovirus P5 promoter is preferably homologous to the AAV serotype which provides the rep and cap gene sequences. Alternatively, the promoter may be a P5 promoter from another AAV type than that which provides the rep and cap sequences. AAVs known to infect other humans or other animals may also provide the P5 promoter. The selection of the AAV to provide any of these sequences does not limit the invention.

In another preferred embodiment, the promoter for rep is an inducible promoter. As discussed above, inducible promoters include, without limitation, the metallothionine (MT) promoter; the dexamethasone (Dex)-inducible mouse mammary tumor virus (MMTV) promoter; the T7 polymerase promoter system; the ecdysone insect promoter; the tetracycline-repressible system; the tetracycline-inducible system; the RU486-inducible system; and the rapamycin-inducible system. One preferred promoter for rep expression is the T7 promoter. The vector comprising the rep gene regulated by the T7 promoter and the cap gene, is transfected or transformed into a cell which either constitutively or inducibly expresses the T7 polymerase. See WO 98/10088, published Mar. 12, 1998.

The spacer is an optional element in the design of the vector. The spacer is a DNA sequence interposed between the promoter and the rep gene ATG start site. The spacer may have any desired design; that is, it may be a random sequence of nucleotides, or alternatively, it may encode a gene product, such as a marker gene. The spacer may contain genes which typically incorporate start/stop and polyA sites. The spacer may be a non-coding DNA sequence from a prokaryote or eukaryote, a repetitive non-coding sequence, a coding sequence without transcriptional controls or coding sequences with transcriptional controls. Two exemplary sources of spacer sequences are the λ phage ladder sequences or yeast ladder sequences, which are available commercially, e.g., from Gibco or Invitrogen, among others. The spacer may be of any size sufficient to reduce expression of the rep78 and rep68 gene products, leaving the rep52, rep40 and cap gene products expressed at normal levels. The length of the spacer may therefore range from about 10 bp to about 10.0 kbp, preferably in the range of about 100 bp to about 8.0 kbp. To reduce the possibility of recombination, the spacer is preferably less than 2 kbp in length; however, the invention is not so limited.

Exemplary molecules providing the AAV rep and cap proteins are plasmids, e.g., pMT-Rep/Cap, pP5-Rep/Cap and pMMTV-Rep/Cap. These plasmids each contain a neomycin selective marker gene and express the AAV rep/cap genes driven by either their native P5 promoter (pP5-Rep/Cap), the zinc-inducible sheep metallothionine promoter (pMTRep/Cap), or the dexamethasone (Dex)-inducible mouse mammary tumor virus (MMTV) promoter (pMMTV-Rep/Cap). Although these proteins may be provided to the cell by various means, exemplary methods of the invention include use of various plasmids. For construction of plasmid pMT-Rep/Cap, the ORF6 sequence was removed from a pMTE4ORF6 plasmid [G. P. Gao et al, *J. Virol.*, 70:8934–8943 (1996)] by BamHI digestion and replaced with a 4.1 kb rep/cap fragment which was prepared by PCR amplification using pSub201 plasmid [Samulski, R. J. et al., *J. Virol.*, 63:3822–3828 (1989)] as a template. Plasmid pMMTV-Rep/Cap was constructed in the same way as pMT-Rep/Cap, except that a pMMTVE4ORF6 plasmid [Gao et al, cited above] was used as the vector backbone. For construction of P5-Rep/Cap, the MT promoter and ORF6 sequences were removed from a pMTE4ORF6 plasmid [G. P. Gao et al, *J. Virol.*, 70:8934–8943 (1996)] by EcoRI/BamHI digestion and replaced with a 4.3 kb P5-Rep/Cap fragment which was isolated from a pSub201 plasmid [Samulski, R. J. Et al, *J. Virol.*, 63:3822–3828 (1989)] by XbaI digestion. Plasmid construction involved conventional genetic engineering methods, such as those described in Sambrook et al, cited above. All of the above-cited references are incorporated by reference herein.

A variety of other plasmid constructs providing the rep and cap proteins are known in the art and may be employed in the host cell of the invention. For example, the rep/cap constructs may omit the spacer between the promoter and the rep/cap genes referred to in the construct described above. Other constructs of the art, such as that described in U.S. Pat. No. 5,622,856, which places the P5 promoter 3' to the rep/cap genes, may also be employed in this context.

The molecule providing the rep and cap proteins may be in any form which transfers these components to the host cell. As exemplified herein, this molecule is preferably in the form of a plasmid, which may contain other non-viral sequences, such as those for marker genes. This molecule does not contain the AAV ITRs and generally does not contain the AAV packaging sequences. To avoid the occurrence of homologous recombination, other virus sequences, particularly those of adenovirus, are avoided in this plasmid. This plasmid is desirably constructed so that it may be stably transfected into a cell.

Although the molecule providing rep and cap may be transiently transfected into the host cell, it is preferred that the host cell be stably transformed with sequences necessary to express functional rep/cap proteins in the host cell, e.g., as an episome or by integration into the chromosome of the host cell. Depending upon the promoter controlling expression of such stably transfected host cell, the rep/cap proteins may be transiently expressed (e.g., through use of an inducible promoter).

The methods employed for constructing embodiments of this invention are conventional genetic engineering or recombinant engineering techniques such as those described in the references above. While this specification provides illustrative examples of specific constructs, using the information provided herein, one of skill in the art may select and design other suitable constructs, using a choice of spacers, P5 promoters, and other elements, including at least one translational start and stop signal, and the optional addition of polyadenylation sites.

B. Host Cells

The mammalian host cell itself may be selected from any mammalian species, such as human cell types, including, without limitation, cells such as A549, WEHI, 3T3, 10T1/2, BHK, MDCK, COS 1, COS 7, BSC 1, BSC 40, BMT 10, VERO, WI38, HeLa, 293 cells (which express functional adenoviral E1), Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc. The requirements for the cell used is that it must not carry virus gene which could result in homologous recombination of a contaminating virus during the production of rAAV; and it must be capable of transfection of DNA and expression of the transfected DNA.

In a preferred embodiment, the host cell is one that has rep and cap stably transfected in the cell, such as the B50 cell line. Other stable rep/cap expressing cell lines, such as those described in U.S. Pat. No. 5,658,785, may also be similarly employed. In another suitable embodiment, the host cell is stably transfected with the sequences necessary to express any adenoviral gene products necessary for replication of rAd/AAV hybrid virus lacking from the hybrid virus.

For example, where the rAd/AAV hybrid virus lacks the adenoviral E4 ORF6 sequence, the selected cell line is engineered to be stably transfected with the sequences necessary for expression of the E4 ORF6 protein. In such an instance, the cell line is preferably one which contains the sequences for expression of rep/cap. Following infection of the cell by the rAd/AAV, the E1a and E1b functions expressed by the hybrid virus turn on expression of the rep/cap functions by the host cell. Thereafter, E4 ORF6 expression is desirably turned on by supplying the agent necessary to induce the promoter controlling E4 ORF6 function to express E4 ORF6 gene product.

As discussed herein, this invention may utilize cells of the following illustrative embodiments:

(a) a cell stably transfected with the AAV rep and cap genes (or functional fragments thereof) and the adenovirus E4 ORF6 gene product;

(b) a cell stably transfected with the AAV rep and cap genes (or functional fragments thereof), the adenovirus E2a gene product and the adenovirus E4 ORF6;

(c) a cell stably transfected with the AAV rep and cap genes (or functional fragments thereof) carried on an episome or integrated into the chromosomes of the cell and transiently expresses the adenovirus E2a gene products;

(d) a cell stably transfected with at least one of the AAV rep and cap genes and the adenovirus E2a gene products (or functional fragments thereof); and (e) a cell stably transfected with the AAV rep gene, the AAV cap gene, E2a gene (or functional fragments thereof) stably as one or more episomes or as integrated DNA, and which transiently expresses the transgene-containing nucleic acid molecule.

Where the host cell and rAd/AAV hybrid virus do not supply the necessary rep and/or cap sequences and any required adenoviral sequences, these sequences may be introduced into the host cell by any suitable method, including, for example, transfection, electroporation, liposome delivery, membrane fusion techniques, high velocity DNA-coated pellets, viral infection and protoplast fusion.

For example, if neither the host cell line nor the rAd/AAV hybrid virus of the invention expresses the E2a gene product, the adenovirus DNA which expresses the E2a gene product may be provided to the host cell in the form of a nucleic acid sequence which also includes a promoter directing the expression of the E2a gene product and other optional regulatory components. The promoter for E2a may be a constitutive, inducible or native promoter, as discussed above. While the promoter in control of the expression of the E2a gene product may be a constitutive promoter in certain embodiments, in one preferred embodiment, the promoter be an inducible promoter so as to control the amount and timing of E2a gene product generation (which is toxic to the cell upon over-accumulation [D. Brough et al, *Virology*, 190:624–634 (1992) and D. Klessig et al, *Virus Res.*, 1:169–188 (1984)]) relative to the production of the E1 gene products. One preferred embodiment provides that the promoter directing the production of E2a be a different inducible promoter from that directing the expression of E1a and E1b, and be inducible by exposure to a different inducing agent than that used for the E1 inducible promoter.

Introduction of a nucleic acid molecule (a plasmid or virus) into the host cell and the preparation of a host cell useful in this invention may also be accomplished using techniques known to the skilled artisan and as discussed throughout the specification. Techniques for construction of nucleic acid molecules include cDNA and genomic cloning, which is well known and is described in Sambrook et al. and Ausubel et al., cited above, use of overlapping oligonucleotide sequences of the adenovirus and AAV genomes, combined with polymerase chain reaction, synthetic methods, and any other suitable methods which provide the desired nucleotide sequence. In preferred embodiment, standard transfection techniques are used, e.g., $CaPO_4$ transfection or electroporation, and/or infection by hybrid adenovirus/AAV vectors into cell lines such as the human embryonic kidney cell line HEK 293 (a human kidney cell line containing functional adenovirus E1 genes which provides trans-acting E1 proteins) and the B50 cell lines (a HeLa cell line containing stably integrated rep and cap genes.

D. Methods for Production of rAAV

As described above, the invention provides a method for producing recombinant adeno-associated virus (rAAV) in the absence of contaminating helper virus or wild-type virus. Suitably, the host cell is infected with the rAd/AAV hybrid virus at a multiplicity of infection in the range of about 0.5 to about 1000 or therebetween, for example, about 1 to about 500, about 10 to about 250, and about 50 to about 200.

The method of producing rAAV virions involves culturing a mammalian host cell containing a rAd/AAV hybrid virus as described herein which contains a rAAV construct to be packaged into a rAAV virion, an AAV rep sequence and an AAV cap sequence under the control of regulatory sequences directing expression thereof. Thereafter, the recombinant AAV virion which directs expression of the transgene is isolated from the cell or cell culture in the absence of contaminating helper virus or wildtype AAV.

Conventional techniques employed in this method include cloning of the rAAV viral genomes, and methods of measuring signal generation, and the like. No purification step is needed to detect message or signal or to separate the rAAV from other viruses. Generally, in production, conventional purification techniques such as chloride gradient centrifugation or column chromatography are used to concentrate the rAAV from the cellular proteins in the lysate. For example, the cells together with transfection medium are harvested by scrapers and subjected to three rounds of freezing-thawing in ethanol-dry ice and 37° C. water bath. The cells may be centrifuged, e.g., for 15 minutes at 4° C.

Because the hybrid Ad/AAV virus of the invention is replication-competent, following infection of the selected host cells, in order to optimize production of rAAV virions, it may be desirable to control the ability of the rAd/AAV hybrid virus to replicate, thereby enhancing the ability of AAV construct to be rescued and packaged into a rAAV virion. The ability of the rAd/AAV hybrid virus to replicate following infection may be inhibited by a variety of approaches which will be readily apparent to those of skill in the art.

For example, in one particularly suitable embodiment, the host cell is infected with the rAd/AAV hybrid virus containing a temperature sensitive mutation in an adenoviral gene necessary for adenoviral replication and/or packaging (e.g., adenoviral gene E2b) at an MOI of about 100 to about 200. Thereafter, the host cell is cultured at a temperature of about 32° C. to about 37° C. and rAAV isolated as described herein. As illustrated in the examples below, this method has been found to provide superior yields of rAAV. One example of a suitable rAd containing a temperature-sensitive mutation is sub100r, which has been described [Schaack, J., et al, *J. Virol.*, 69:4079–4085 (1995)].

Additionally, or alternatively, expression of one or more the adenoviral genes necessary for replication of the rAd/AAV may be controlled. For example, the adenoviral E4 (or E4 ORF6) is expressed under the control of an inducible promoter, by the rAd/AAV or by the host cell where the rAd/AAV hybrid virus does not express this gene product. In another example, the adenoviral E1 and E2a gene products are expressed under the control of at least one inducible promoter. Thus, this method further includes the step of contacting the cultured host cells with at least one inducing agent, which controls the expression of at least one of the required adenovirus gene products. Where each required adenovirus gene product is under control of a different inducible promoter, the method further entails the steps of adding to the host cell culture a first inducing agent for the first inducible promoter and a second inducing agent for the second inducible promoter. This embodiment of the method thus permits controlled expression of the adenoviral gene products, e.g., adenoviral genes E1a, E1b, E2a, and/or E4 ORF6. Further, this invention permits expression of the adenoviral gene products (e.g., E1 and E1b) in a desired ratio to the expression of the other adenoviral gene product(s) (e.g., E2a) which is optimal for rAAV production in the particular host cell under suitable culture conditions for that cell.

The determination of a suitable ratio of E1 gene products to E2a gene products and the AAV rep/cap products may be accomplished by one of skill in the art, taking account of the cell type, the strength of constitutive and/or inducible promoters used, the amounts of inducer(s) used, and the order or timing of induction of preferred gene products. The optimal ratio which permits the greatest production of rAAV may differ as these factors differ. For example, where the E1a gene is controlled by a weak or medium strength constitutive promoter, the E2a gene should be controlled by a strong inducible promoter and the inducing agent added early in the culture to obtain a suitable ratio. Where the E1a gene is controlled by an inducible promoter as well as the E2a gene, the two inducing agents may be added in varying amounts and at varying orders of induction to provide the optimal production system for rAAV. However, such optimization experimentation employed to determine preferred amounts and orders is well within the skill of the art and is merely routine in light of the disclosures herein.

In another preferred embodiment of the method, the E1a gene product is expressed under the control of an inducible promoter and the E1b and E2a genes, as well as any other adenoviral genes (e.g., E4ORF6 and/or VAI RNA) that are present, are expressed under the control of their native promoter. As discussed above, the E1a gene product activates the native promoters of E1b, E2a and any other adenoviral genes. Any inducible promoter can be used so long as expresses low basal levels of E1a when the cell is uninduced and high levels of E1a when the cell is contacted with an inducing agent. A number of inducible promoters are known in the art and have been discussed throughout the specification. Specific inducible promoters include, without limitation, the zinc-inducible sheep metallothionine (MT) promoter; the dexamethasone (Dex)-inducible mouse mammary tumor virus (MMTV) promoter; the ecdysone insect promoter; the tetracycline-repressible system; the tetracycline-inducible system; the RU486-inducible system; and the rapamycin-inducible system.

The following examples illustrate several preferred methods of the invention. These examples are illustrative only and are not intended to limit the scope of the invention.

EXAMPLE 1
Use of the B-50 Cell Line and Ad/AAV Hybrid Vector for Production of a Helper Independent Cell Line A recombinant Ad/AAV hybrid vector is constructed using the methods described in U.S. Pat. No. 5,856,152 except that the E3 gene is deleted and the E1 gene operably linked to and under the control of the RSV or PGK promoter is cloned into the E3 region of the adenovirus genome. The Ad/AAV hybrid vector is packaged as described in U.S. Pat. No. 5,856,152.

Briefly described, B-50 is a cell which stably expresses AAV type 2 rep and cap genes under the control of the homologous p5 promoter. This cell line is characterized by integration of multiple copies (at least 5 copies) of P5-rep-cap gene cassettes in a concatamer form into the host chromosome. This B-50 cell line was deposited with the American Type Culture Collection, 10801 University Boulevard, Manassas, Va. 20110-2209 on Sep. 18, 1997 under Accession No. CRL-12401 pursuant to the requirements of The Budapest Treaty on the International Recognition of the Deposit of Microorganisms for the Purposes of Patent Procedure.

B-50 cells are seeded at a density of $2 \times 10^5$ cells per 60 mm plate for 24 hours. Twenty-four hours later, the seeding media (DMEM/10% FBS supplemented with antibiotics) is replaced with DMEM/2% FBS. The cells are infected with recombinant Ad/AAV clone containing E1 and the rAAV minigene at an appropriate MOI. This one step infection of B-50 cells provides all the helper genes required for rAAV production. Thus, there will be no need for other helper viruses such as sub100r.

Figure 1B:
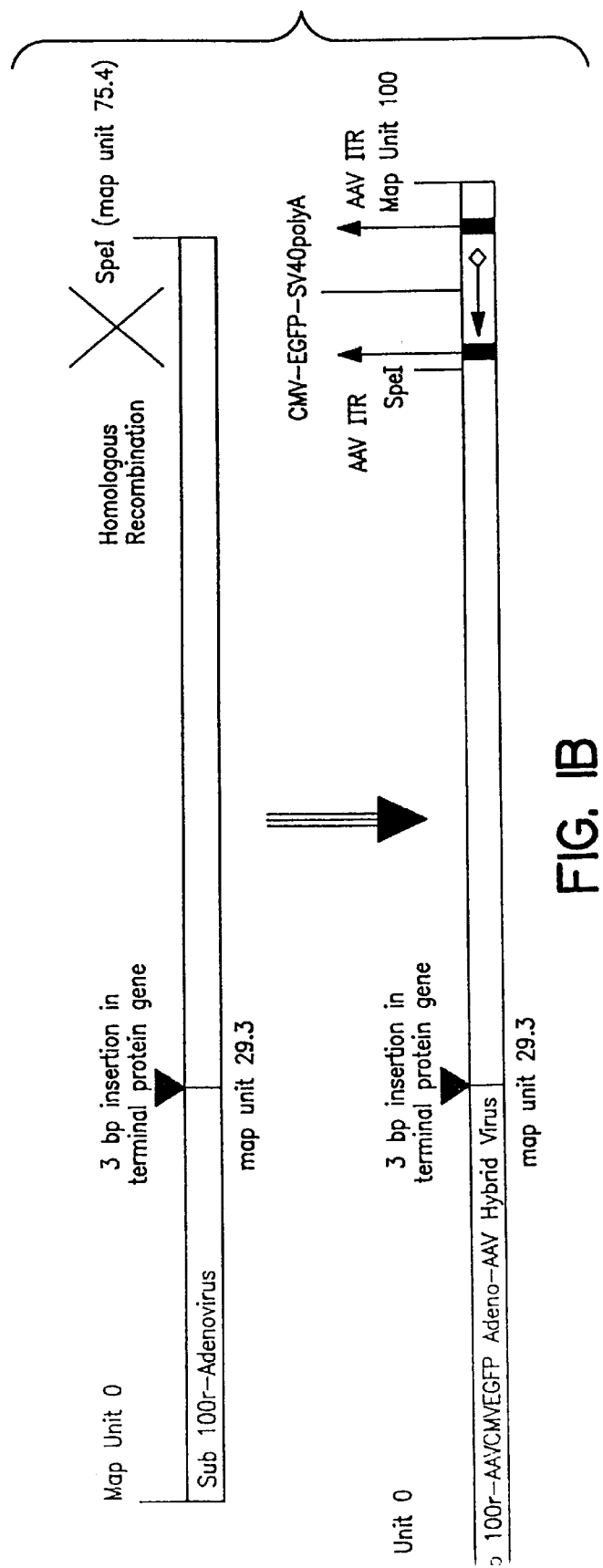

Twenty-four hours to ninety-six hours after infection, the cell lysates are prepared and the lysate is titered for rAAV production by any process known in the art. If the rAAV is rAAVLacZ, the lysate can be titered as follows. The cells together with transfection medium are harvested by scrapers and subjected to three rounds of freezing-thawing in ethanol-dry ice and 37° C. water bath. The cells are centrifuged at 3000 rpm in a table top centrifuge for 15 minutes at 4° C. One tenth of each lysate is used to infect 84-31 cells, an E1/E4-double complementing cell line which is transducible by rAAV, for 24 hours. The 84-31 cells are then histochemically stained with X-Gal. The numbers of blue cells in each infection are scored and presented on the Y-axis of FIG. 1 as Infectious Units (IU, 1 IU was defined as one blue cell counted) of rAAVLacZ produced in each transfection.

EXAMPLE 2
Production of rAAV in B50 Cells by Replication Competent Ad-AAV Hybrid Virus A rAAVCMVGFP genome in which a Green Fluorescent Protein (GFP)reporter gene is driven by CMV promoter and flanked by AAV2 ITRs was cloned into the E3 region of an Ad5 mutant, sub100r virus. The E2b terminal protein gene of sub100r was disrupted by a 3 bp insertion, rendering a temperature sensitive phenotype. The resulting recombinant Ad-AAV hybrid is a genotypically wild type for E1, E2a, E4 and VARNA genes but its E3 genes are now replaced with a rAAVCMVGFP genome. Thus this second generation Ad-AAV hybrid possesses all essential helper genes and a rAAV genome and, theoretically, a single infection of B50 cells with the virus should lead to rescuing, replicating and packaging of rAAV genomes.

A. Construction of a Replication-competent rAd-AAV Hybrid Virus

A commercially available plasmid construct pAB27 was purchased from Microbix Biosystems (Ontario, Canada). It carries the following segments of the Ad5 genome: m.u. 0–1, 10.6–16.1, and 69–100 with a 2.7 kb E3 deletion spanning m.u. 78.3 n 85.8. A recombinant AAVCMVGFP genome was isolated from the prAAVCMVGFP construct as a PVU II fragment and cloned in to Sca I site of pAB27 plasmid. The resulting shuttle plasmid was designated as pABrAAVCMVEGFP. On the other hand, an Ad E2B terminal protein mutant, sub100r was chosen as viral backbone to build up the new Ad-AAV hybrid that is conditionally replication competent at its permissive 32° C. To introduce the rAAVCMVEGFP into the sub100r genome, sub100r viral DNA was digested with restriction endonuclease Spe I and co-transfected with pABrAAVCMVEGFP into 293 cells by calcium phosphate method. The transfected cells were overlaid with top agar and cultured at 32° C. for 14 days. The green viral plaques of sub100r-rAAVCMVGFP were isolated for further plaque purification and expansion to a large-scale viral prep. Please see the FIG. I for cloning of pABrAAVCMVGFP construct and illustration of the homologous recombination process to generate subr100rAAVCMVGFP hybrid virus.

B. Production of rAAV

B50 cells were seeded in 12 well plates at a density of $1 \times 10^5$ cells per well. Twenty-four hours later, the cells were infected with the sub100rAAVCMVGFP hybrid at 100, 1000, 2000, and 4000 viral particles per cell. For each infection, triplicates of 12 well plates were set up for incubation at different temperatures, 32, 37 and 39.5° C. As positive controls, B50 cells in 12 wells were infected with wild type Ad5 helper and sub100rAAVCMVGFP at the MOIs described above either simultaneously or with a 24 hr interval. At 72, 96 and 120 hr post infection, total cell lysate of each infection was harvested. After have gone through three cycles of freeze/thaw, the lysate was spun at 3000 rpm and 4° C. for 15 min. The resulting supernatant of each sample was collected and stored at −80° C. For quantifying rAAVCMVGFP produced in each infection, a portion of each sample was heated at 56° C. for 1 hr to inactivate infectious Ad-AAV hybrid sub100-rAAVCMVGFP and put onto 84-31 cells, a E1/E4 complementing cell clone, in serial dilution. Green Fluorescent Forming Units (GFFU) of each sample were scored under an UV-microscope at 24–48 hr post infection and computed as GFFU per B50 cell used in the initial sub100rAAVCWGFP infection. One GFFU here was defined by the foci of GFP transduction by rAAVCM-VGFP virus in a limiting-dilution infection. Thus GFFUs per cell represent rAAVCMVGFP produced by each B50 cell under the corresponding experiment set-up.

C. Optimization of Using Replication-competent rAd-AAV Hybrid for AAV Production in B50 Cells A series of experiments were set up to optimize conditions for maximum yield of rAAV produced by this new B50/hybrid system and compare with the original B50/hybrid system.

The B50/Replication competent hybrid infection system can produce about 1/3–1/6 of rAAVCMVGFP produced in the presence of Ad helper virus in the initial experiment. The data summarized in the Table 1 demonstrated the feasibility of using the B50/replication competent Ad-AAV hybrid infection system for rAAV production.

TABLE 1

Results of initial prove of concept experiment
Experiment Set-Up Yield of rAAVCMVGFP per cell

|  | 72 hr | 96 hr | 120 hr |
|---|---|---|---|
| Ad5 Wt + sub100rAAVCMVGFP, 24 hr interval at 37° C. (positive control) | | | |
| 100 pts each per cell | 360 | 292 | 260 |
| 1000 pts each per cell | 356 | 288 | 200 |
| 2000 pts each per cell | 136 | 124 | 100 |
| 4000 pts each per cell | 44 | 40 | 24 |
| sub100rAAVCMVGFP only at 37° C. | | | |
| 100 pts each per cell | 13.2 | 66 | 70.4 |
| 1000 pts each per cell | 4.6 | 10.4 | 9.3 |
| 2000 pts each per cell | 0.5 | 1.1 | 1.3 |
| 4000 pts each per cell | 0.8 | 1.5 | 3.7 |
| sub100rAAVCMVGFP only at 32° C. | | | |
| 100 pts each per cell | 0.44 | 10 | 50 |
| 1000 pts each per cell | 0.6 | 1A | 12.8 |
| 2000 pts each per cell | 1.5 | 2.0 | 7.2 |
| 4000 pts each per cell | 1.7 | 3.2 | 3.6 |
| sub100rAAVCMVGFP only at 39.5° C. | | | |
| 100 pts each per cell | 0.1 | 0.1 | 0.2 |
| 1000 pts each per cell | 2.1 | 2.4 | 2.7 |
| 2000 pts each per cell | 1.6 | 1.4 | 0.6 |
| 4000 pts each per cell | 1.8 | 1.8 | 1.2 |

The data presented here suggest that, under the experiment conditions tested, the B50/replication competent Ad-AAV hybrid system can produce rAAV. But the maximum yield went down 3–6 folds as compared to the positive where B50 cells were infected with an Ad5Wt helper and the hybrid with a 24 hr interval. The single infection system performed a lot better at 32 and 37° C. as compared to 39.5° C.

We hypothesized that, once entered B50 cells, replication competent Ad-AAV hybrid faces two possible fates: either to be replicated or to be crippled by Rep proteins for AAV rescuing, replicating and packaging. A productive infection for rAAV using this system will be a delicate balance of both directions. We have previously demonstrated that, for high yield AAV production by the B50/Ad helper/E1-deleted Ad-AAV hybrid, there is a critical temporal relationship among Rep/cap gene expression triggered by Ad5 E1 proteins, transient amplification of incoming Ad-AAV hybrids, resolving of rAAV genomes from the hybrid backbone and further replication of AAV genomes, Although the permissive temperature for sub100r mutant is 32° C., it is known that such temperature sensitivity is somewhat leaky at 37° C. but quite stringent at 39.5° C. We expected that, at 37° C., replication of sub100rAAVCMVGFP would be slowed down but expression of Rep/cap, AAV rescuing, replication and packaging would be optimal. The data demonstrated that the system was indeed more productive at 37° C. as compared to 32° C. But AAV productivity at 39.5° C. was sharply decreased. In this case, there was probably no hybrid replication at all. Additionally, the whole cellular machinery was under high temperature stress, resulting in deficiency in rep/cap expression, AAV rescuing, replication and packaging.

1. Defining Optimal Multiplicity of Infection for sub100rAAVCMVGFP

Based on the data from Example 2B, infection of B50 cells at lower MOIs appears to be beneficial to production of AAV. According to the data from the initial experiment, it appears that, at productive temperatures, 32 and 37° C., yield of rAAV drops sharply as the MOI of sub100rAAVCMVGFP infection increases. There is a dramatic difference in AAV productivity between 100 pts/cell and 1000 pts/cell, suggesting that the optimal MOI for maximum productivity lie in that range. To define the optimal MOI, the second experiment carried out was to examine impact of MOI between 20 and 1.000 particles (pt)/cell at both 32 and 37° C. (Table 2). Accordingly, B50 cells were seeded in 12 well plates as described above and infected with 20, 40, 100, 200, 400, and 1000 particles of sub100rAAVGFP. The crude cell lysate samples were prepared and assayed for rAAVCMVGFP productivity per cell in the same way as above.

TABLE 2

Optimization for MOI
Experiment Set-up rAAVCMVGFP Yield (GFFU/cell)

|  | 72 hr | 96 hr | 120 hr | 144 hr |
|---|---|---|---|---|
| sub100rAAVCMVGFP at 32° C. | | | | |
| 20 pts/cell | 0 | 0.4 | 22.1 | 26.0 |
| 40 pts/cell | 0 | 0.4 | 17.2 | 30.7 |
| 100 pts/cell | 0.1 | 2.3 | 40.7 | 86.7 |
| 200 pts/cell | 0.1 | 7.8 | 26.5 | 80.6 |
| 400 pts/cell | 0 | 9.9 | 21.4 | 22.7 |
| 1000 pts/cell | 0.2 | 1.7 | 4.6 | 8.2 |
| sub100rAAVCMVGFP at 37° C. | | | | |
| 20 pts/cell | 0.6 | 2.9 | 2.5 | 5.0 |
| 40 pts/cell | 0.7 | 8.8 | 14.5 | 16.4 |
| 100 pts/cell | 4.2 | 20.6 | 27.7 | 34.7 |
| 200 pts/cell | 10.1 | 39.5 | 62.0 | 111.3 |
| 400 pts/cell | 6.7 | 21.0 | 27.1 | 36.3 |
| 1000 pts/cell | 2.1 | 9.0 | 4.2 | 12.8 |
| AdsWt + sub100rAAVCMVGFP, a 24 hr interval, at 37° C. (positive control) | | | | |
| 100 pts/cell | 46.3 | 100.8 | 119.7 | 134.4 |

The results revealed that either 100 or 200 pts/cells was optimal for the infection at 32° C. But the situation at 37° C. was quite different where the optimal MOI was restrictively limited at 200 pts/cell. Two folds of increase or decrease of the MOI resulted in a 60% reduction in AAV productivity. The impact of MOI on AAV production observed here and in previous study demonstrated the importance of reaching a delicate balance between hybrid replication and rAAV packaging in using B50/hybrid system for AAV production. It is well known that adenovirus replication process is highly MOI dependent, particularly under permissive and semi-permissive conditions. It is plausible that, at high MOIs, hybrid virus replication become dominant but rAAV rescuing, replicating and packaging diminish significantly. On the other hand, limited hybrid virus amplification is desirable for increasing the number of rAAV genomes for rescuing and packaging. This is clearly demonstrated in the results presented in Table 2. Since 32° C. is permissive to sub100rAAVCMVGFP, there was no obvious difference in AAV yield observed between 100 and 200 pts/cell. Only when MOI exceeds 400 pts/cell, then AAV yield went down dramatically. However, when infections were carried out at a semi-permissive temperature 37° C., optimal MOI was restricted at 200 pts/cell only. Here, a limited and MOI dependent hybrid virus replication became critical to maximum AAV packaging.

2. Defining Optimal Temperature for the Single Infection with sub100rAA VGFP

From the initial experiment, it was found that there was very little AAV produced at 39.5° C. but AAV productivity at 32 and 37° C. was comparable. To investigate potential impact of infection temperatures on AAV productivity, the MOI experiment described above was run in duplicates at both 32 and 37° C.

The data presented in Tables I and 2 also indicated that, at optimal MOIs, AAV production was better at 37° C. than 32° C. This could also be explained by the need for balancing between limited hybrid virus replication and AAV rescuing, replicating and packaging. Apparently, at the semi-permissive temperature 37° C., the equilibrium of two different events moved towards in favor of AAV packaging, leading to higher productivity.

3. Switch of the Temperature from 37 to 32° C. During the Infection Process

B50 cells in 12 well plates were infected with sub100rAAVCMVGFP at 100 particles per cell and 37° C. for 36 and 60 hr. Then the plates were moved to another incubator set at 32° C. The crude cell lysate was prepared at 72, 96, 120, 144 and 168 hr post infection for titration of AAV productivity on 84-31 cells.

The logic behind this experimental design was that sub100rAAVCMVGFP virus should have limited replication at 37° C. but activation of P5 promoter for Rep/cap protein should be optimal. A 24 hr incubation at 37° C. would allow Rep/cap expression initiated with limited level of hybrid virus replication and thus get B50 cells conditioned for AAV rescuing, replicating and packaging. Once the infection was switched to 32° C., hybrid virus replication should also slow down somewhat by inhibition effects of Rep proteins accumulated in the cells. The results of the temperature switch experiment (Table 3) did not meet the expectation probably due to the failure to achieve an optimal balance between hybrid replication and AAV rescuing and replicating. But the data did indicate that an earlier switch in temperature gave rise to a better yield than a later one, suggesting timing of the switch play crucial role in AAV production.

TABLE 3

Temperature switching and rAAV productivity

| Experiment Set-up | rAAVCMVGFP Yield-(GFFU/cell) | | | | |
|---|---|---|---|---|---|
| | 72 hr | 96 hr | 120 hr | 144 hr | 168 hr |
| Sub100rGFP, 100 pts/cell (37° C. for 36 hr then switching to 32° C.) | 00.36 | 0.4 | 6.3 | 15.1 | 50.4 |

TABLE 3-continued

Temperature switching and rAAV productivity

| Experiment Set-up | rAAVCMVGFP Yield-(GFFU/cell) | | | | |
|---|---|---|---|---|---|
| | 72 hr | 96 hr | 120 hr | 144 hr | 168 hr |
| Sub100rGFP,100 pts/cell (37° C. for 60 hr then switching to 32° C.) | 1.76 | 4.4 | 15.1 | 15.5 | 16.6 |
| Ad5Wt + sub100rAAVCMVGFP (100 pts/cell, a 24 hr interval, 37° C., positive control) | 46.3 | 100.8 | 119.7 | 134.4 | 88.2 |

4. Addition of a Second Batch of sub100rAAVCMVGFP to B50 Cells at 24 Hr Post the Initial Infection B50 cells in 12 well plates were infected with sub100rAAVCMVGFP at 100 particle per cell and 37° C. for 24 hr. A second batch of sub100rAAVCMVGFP at 100 particle per cell was added to 37° C. and the other set was moved to a 32° C. incubator. AAV production under each condition was examined at 72, 96, 120, 144 and 168 hr post the initial infection.

In the classical B50/Ad5 helper/E1-deleted Ad-AAV hybrid system, it was essential to have a 24 hr interval between the first Ad helper virus infection and the second Ad-AAV hybrid infection. This delicate temporal relation of two infections allows creation of optimal cellular conditions, such as proper level of Rep proteins to regulate appropriate rate of hybrid virus replication and AAV rescuing, for high yield of AAV production. In that case, the difference between Ad helper virus and E1-deleted hybrid infections is the presence and absence of E1 proteins. However, when replication competent Ad-AAV hybrid is used for AAV production in B50 cells, there is no difference between Ad helper virus and the hybrid in terms of their ability to provide all necessary helper functions. If we infect the cells with two batches of the hybrid with a 24 hr of interval, the first batch should serve as a helper just like Ad Wt infection and the second batch would be just like E1-deleted hybrid to deliver rAAV genomes for amplification, rescuing and packaging. We would expect AAV productivity of 850/ replication competent Ad-AAV hybrid method to be as high as that of classical B50/hybrid system. The data generated from the experiment was indeed supportive to OUT theory (Table 4). Since only one type of Adenovirus used in this new production method, it simplifies our purification process somewhat and eases the scaling-up process. Furthermore, we could introduce some more severe mutations such as E4 deletion into the hybrid backbone and corresponding Ad genes into B50 cells stably. Thus we disable the hybrid virus itself so that even if AAV preps were contaminated with some defective hybrids, side effects of such defective hybrids in vivo would be further minimized.

TABLE 4

Improvement of rAAV productivity by a double infection Process with a single virus, sub100rAAVCMVGFP

| Experiment Set-up | rAAVCMVGFP Yield (GFFU/cell) | | | | |
|---|---|---|---|---|---|
| | 72 hr | 96 hr | 120 hr | 144 hr | 168 hr |
| Sub100AAVCMVGFP + (a 24 hr interval, 100 pts/cell at each infection, | 0.76 | 8.7 | 109.2 | 135.5 | 88.2 |

TABLE 4-continued

Improvement of rAAV productivity by a double infection Process with a single virus, sub100rAAVCMVGFP
Experiment Set-up rAAVCMVGFP Yield (GFFU/cell)

|  | 72 hr | 96 hr | 120 hr | 144 hr | 168 hr |
|---|---|---|---|---|---|
| 37° C.) Sub100AAVCMVGFP + Sub100AAVCMVGFP (a 24 hr interval, 100 pts/cell at each infection, 37° C. for 24 hr, switch to 32° C. after 2$^{nd}$ infection) | 9.0 | 45.2 | 44.1 | 54.6 | 34.7 |
| Ad5Wt + sub100rAAVCMVGFP (100 pts/cell, a 24 by interval, 37° C., positive control) | 46.3 | 100.8 | 119.7 | 134.4 | 88.2 |

All documents cited above are herein incorporated by reference. Numerous modifications and variations of the present invention are included in the above-identified specification and are expected to be obvious to one of skill in the art. Such modifications and alterations to the processes of the present invention are believed to be encompassed in the scope of the claims appended hereto.

What is claimed is:

1. A method for producing recombinant adeno-associated virus (rAAV) comprising the step of:
    culturing a host cell comprising:
    (a) an AAV rep sequence and an AAV cap sequence under the control of regulatory sequences directing expression thereof; and
    (b) an adenovirus/AAV hybrid virus comprising a recombinant adeno-associated virus (rAAV) vector and nucleic acid sequences encoding adenovirus E1a and adenovirus E1b under the control of regulatory sequences directing expression of the E1a and E1b gene products, wherein said hybrid virus contains sufficient adenoviral sequences to permit replication of said hybrid virus in a host cell.

2. The method according to claim 1, further comprising the step of isolating the rAAV from said host cell or host cell culture.

3. The method according to claim 1, wherein the host cell is stably transformed with the AAV rep sequence.

4. The method according to claim 1, wherein the host cell is stably transformed with the AAV cap sequence.

5. The method according to claim 1, wherein the rep sequence is transiently expressed in the host cell.

6. The method according to claim 1, wherein the cap sequence is transiently expressed in the host cell.

7. A method according to claim 1, further comprising the step of, prior to culturing, infecting the host cell with the hybrid adenovirus/AAV at a multiplicity of infection of about 0.5 to about 1000.

8. The method according to claim 1, wherein the hybrid adenovirus/AAV further comprises a temperature-sensitive mutation in the adenovirus E2b gene.

9. The method according to claim 1, wherein the hybrid adenovirus/AAV is cultured at a temperature of about 32° C. to about 37° C.

10. The method according to claim 1, wherein the adenovirus/AAV hybrid virus further comprises a functional deletion in the E3 region.

11. The method according to claim 1, wherein the adenovirus/AAV hybrid virus further comprises a non-functional deletion of adenoviral coding sequences in the E4 region, wherein said hybrid virus contains the E4 ORF6 region.

12. The method according to claim 1, wherein the E1a and E1b nucleic acid sequences are located in the site of the wild-type E3 region of the adenovirus/AAV hybrid virus.

13. The method according to claim 1, wherein the rAAV vector is located in the wild-type adenoviral E1a and E1b region of the adenovirus/AAV hybrid virus.

14. The method according to claim 1, wherein the AAV vector in the adenovirus/AAV hybrid virus comprises AAV 5' and 3' inverted terminal repeats (ITRs) and a transgene under the control of regulatory sequences directing expression thereof.

15. The method according to claim 1, wherein the regulatory sequences in the adenovirus/AAV hybrid virus comprise a first promoter which directs the expression of the E1a gene product.

16. The method according to claim 15, wherein the first promoter in the adenovirus/AAV hybrid virus is selected from the group consisting of a native promoter of E1a, an inducible promoter, a tissue-specific promoter, and a constitutive promoter.

17. The method according to claim 15, wherein the regulatory sequences in the adenovirus/AAV hybrid virus comprise a second promoter which directs the expression of the adenoviral E1b gene product.

18. The method according to claim 17, wherein the second promoter in the adenovirus/AAV hybrid virus is identical to the first promoter.

19. The method according to claim 17, wherein the second promoter and the first promoter in the adenovirus/AAV hybrid virus are different.

20. A method for producing recombinant adeno-associated virus (rAAV), comprising the step of:
    culturing a host cell containing:
    (a) an AAV rep sequence and an AAV cap sequence under the control of regulatory sequences directing expression thereof; and
    (b) an adenovirus/AAV hybrid virus comprising a recombinant adeno-associated viral (rAAV) vector and nucleic acid sequences encoding adenovirus E1a and adenovirus E1b are under the control of regulatory sequences directing expression of the E1a and E1b gene products, wherein said hybrid virus contains sufficient adenoviral sequences to permit replication of said hybrid virus in a host cell;
    wherein said host cell is cultured under conditions which inhibit hybrid virus replication, resulting in enhanced rAAV production.

21. The method according to claim 20, wherein the adenovirus/AAV virus further comprises a temperature sensitive mutation in the adenoviral E2b gene.

22. A method for producing recombinant adeno-associated virus (rAAV) comprising the step of:
    culturing a host cell comprising:
    (a) an AAV rep sequence and an AAV cap sequence under the control of regulatory sequences directing expression thereof; and
    (b) an adenovirus/AAV hybrid virus comprising:
        (i) adenovirus 5' cis-elements necessary for replication and packaging;

(ii) a deletion of adenoviral sequences in the native adenoviral E1a and E1b region;
(iii) a recombinant adeno-associated viral (rAAV) vector;
(iv) a deletion of adenoviral sequences from the E3 region;
(v) nucleic acid sequences encoding adenovirus E1a and adenovirus E1b under the control of regulatory sequences directing expression of the E1a and E1b gene products, wherein said E1a and E1b nucleic acid sequences are located in the site of the E3 region; and
(vi) adenovirus 3' cis-elements necessary for replication and packaging.

* * * * *

UNITED STATES PATENT AND TRADEMARK OFFICE
CERTIFICATE OF CORRECTION

PATENT NO.   : 6,258,595 B1
DATED        : July 10, 2001
INVENTOR(S)  : Guang-Ping Gao & James M. Wilson It is certified that error appears in the above-identified patent and that said Letters Patent is hereby corrected as shown below:

Column 3,
Line 44, replace "E4 ORF6), which is supplied by the host cell" with -- E4 ORF6), which is supplied by the host cell. --

Column 8,
Line 53, replace "HNF4" with -- HNF-4 --.

Column 10,
Line 41, replace "2:185-96 (1997);" with -- 24:185-96 (1997); --.
Line 42, replace "1:654-64 (1996)]," with -- 11:654-64 (1996)], --.

Column 11,
Line 61, replace "functional fragments thereof," with -- functional fragments thereof. --.

Column 18,
Line 47, replace "subrloorAAVCMVGFP" with -- subloorAAVCMVGFP --.

Column 19,
Line 67, replace "bone and further replication of AAV genomes" with -- bone and further replication of AAV genomes. --.

Column 20, Table 2,
Line 53, replace "AdsWt" with -- Ad5Wt --.

Signed and Sealed this

Twenty-sixth Day of February, 2002

*Attest:*

*Attesting Officer*

JAMES E. ROGAN
*Director of the United States Patent and Trademark Office*